United States Patent [19]

Wu et al.

[11] Patent Number: 5,254,793
[45] Date of Patent: Oct. 19, 1993

[54] ALKYLATION PROCESS AND CATALYST THEREFOR

[75] Inventors: An-hsiang Wu; Marvin M. Johnson, both of Bartlesville, Okla.

[73] Assignee: Phillips Petroleum Company, Bartlesville, Okla.

[21] Appl. No.: 9,504

[22] Filed: Jan. 25, 1993

[51] Int. Cl.$^5$ .............................................. C07C 2/60
[52] U.S. Cl. ................................... 585/726; 502/202; 502/208; 502/217; 585/727; 585/730
[58] Field of Search ............. 502/202, 208, 217, 231; 585/726, 727, 728, 730

[56] References Cited

U.S. PATENT DOCUMENTS

| | | | |
|---|---|---|---|
| 2,824,153 | 2/1958 | Kelly et al. | 585/726 |
| 3,248,343 | 4/1966 | Kelly et al. | 252/442 |
| 3,271,299 | 9/1966 | Kearby | 208/114 |
| 3,873,634 | 3/1975 | Hoffman | 585/726 |
| 3,925,495 | 12/1975 | Rodewald | 585/373 |
| 3,984,352 | 10/1976 | Rodewald | 252/436 |
| 4,025,566 | 5/1977 | Nagai et al. | 502/202 |
| 4,094,922 | 6/1978 | Bartek et al. | 260/671 C |

Primary Examiner—Asok Pal
Attorney, Agent, or Firm—K. K. Brandes

[57] ABSTRACT

A composition of matter, which is an effective alkylation catalyst composition, is prepared by a method comprising heating, at a temperature of about 40°-90° C., (a) aluminum chloride, (b) boron phosphate, (c) alumina and/or silica, and (d) at least one chlorinated hydrocarbon (preferably $CCl_4$), and subsequently separating the formed solid from the chlorinated hydrocarbon. The thus-prepared catalyst composition is employed in the alkylation of $C_2$–$C_7$ alkane(s) with $C_2$–$C_7$ alkene(s).

20 Claims, No Drawings

ALKYLATION PROCESS AND CATALYST THEREFOR

BACKGROUND OF THE INVENTION

In one aspect, this invention relates to the alkylation of alkanes (paraffins) with alkenes (monoolefins). In another aspect, this invention relates to a method of preparing an effective alkylation catalyst.

The use of catalysts containing aluminum chloride as an active component for the alkylation of hydrocarbons is known. The present invention is directed to novel, more effective alkylation catalysts comprising aluminum chloride.

SUMMARY OF THE INVENTION

It is an object of this invention to prepare a novel, solid composition of matter comprising aluminum chloride. It is another object of this invention to provide a novel, solid alkylation catalyst composition of matter comprising aluminum chloride. It is a further object of this invention to employ this novel, solid composition of matter as a catalyst in the alkylation of alkane(s) with alkene(s). Other objects and advantages will be apparent from the detailed description of the invention and the appended claims.

In accordance with this invention, a method of preparing a solid composition of matter (which is effective as a catalyst for the alkylation of alkanes with alkenes) comprises the steps of:

(1) heating for a period of at least about 10 minutes, at a temperature in the range of about 40° C. to about 90° C., in the substantial absence of water: (a) aluminum chloride, (b) boron phosphate, (c) at least one inorganic support material selected from the group consisting of alumina and silica having a surface area (measured by the BET method of Brunauer, Emmett and Teller employing nitrogen) of at least about 50 m$^2$/g, and (d) at least one chlorinated hydrocarbon (i.e., at least one chlorine derivative of a hydrocarbon) having a normal boiling point (i.e., a boiling point at a pressure of about 1 atm.) of about 40°-90° C.; wherein the molar ratio of boron phosphate to aluminum chloride is at least about 0.1:1 and the weight ratio of boron phosphate to the at least one inorganic support material is at least about 0.05:1; and (2) separating the solid component formed in the heated mixture obtained in step (1) from the at least one chlorinated hydrocarbon under a dry gas atmosphere.

In a preferred embodiment, the chlorinated hydrocarbon is carbon tetrachloride. In another preferred embodiment, the molar ratio of BPO$_4$ to AlCl$_3$ is about 0.1:1 to about 1:1. In a further preferred embodiment, the BET surface area (measured by the BET method of Brünatier, Emmett and Teller employing nitrogen) of alumina and/or silica is about 100-400 m$^2$/g. In still another preferred embodiment, the weight ratio of BPO$_4$ to said at least one inorganic support material is about 0.05:1 to about 1:1. In a still further preferred embodiment, step (2) is carried out in two sub-steps: filtering the mixture obtained in step (1) so as to recover the solid component therefrom and subsequently drying the recovered solid material (i.e., substantially removing volatile substances, in particular chlorinated hydrocarbon(s), therefrom. More preferably, heating step (1) is carried out for about 5-30 hours.

Also in accordance with this invention, a composition is provided having been prepared by the above-described preparation method.

Further in accordance with this invention, a process for alkylating alkanes comprises the step of contacting at least one feed alkane (i.e., at least one straight-chain alkane or at least one branched alkane or a mixture thereof) containing about 2-7 carbon atoms per molecule with at least one feed alkene (i.e., at least one straight chain alkene or at least one branched alkene or a mixture thereof) containing about 2-7 carbon atoms per molecule with the catalyst composition having been prepared by the above-described preparation method of this invention, at effective alkylation conditions so as to obtain at least one product alkane containing at least two more carbon atoms per molecule than said at least one feed alkane. Preferably, the at least one feed alkane contains 3-5 carbon atoms per molecule, and the at least one feed alkane contains 3-5 carbon atoms per molecule.

DETAILED DESCRIPTION OF THE INVENTION

Step (1) of the method of preparing catalysts employed in the alkylation process of this invention can be carried out in any suitable manner in any suitable vessel. Generally, substantially dry AlCl$_3$, BPO$_4$, Al$_2$O$_3$ and/or SiO$_2$, and chlorinated hydrocarbon(s) are thoroughly mixed under a dry inert gas atmosphere (N$_2$, He, Ar and the like), and then heated under a dry inert gas atmosphere at a temperature of about 40°-90° C., preferably about 70°-80° C., for a time period of about 4 to about 125 hours, preferably about 10-30 hours, more preferably 15-25 hours. It is preferred to carry out step (1) with agitation, either mechanically (e.g., by means of a stirrer) or ultrasonically.

The molar ratio of BPO$_4$ to AlCl$_3$ should be at least about 0.1:1, and preferably is about 0.1:1 to about 1.0:1 (preferably about 0.15:1 to about 1.0:1). The weight ratio of BPO$_4$ to Al$_2$O$_3$ and/or SiO$_2$ should be at least about 0.05:1, and preferably is about 0.05:1 to about 1.0:1. (more preferably about 0.08:1 to about 0.6:1). Generally, the surface area of the inorganic support material (i.e., alumina or silica or silica/alumina) is at least about 40 m$^2$/g (preferably is about 100-500 m$^2$/g). Generally, the particle size of alumina and/or silica is in the range of smaller than 20 mesh and larger than 200 mesh (preferably in the 20-100 mesh range).

Boron phosphate can be prepared by any suitable method, preferably by the reaction of a boric acid ester B(OR)$_3$ wherein each R can be independently selected from alkyl radicals containing 1-5 carbon atoms (more preferably tri-n-propyl borate) and orthophosphoric acid (H$_3$PO$_4$). Optionally, an inorganic support material (such as alumina and/or silica) can be present during this reaction so as to prepare BPO$_4$ on a silica support.

The at least one chlorinated hydrocarbon employed in step (1) can be one chlorinated hydrocarbon or a mixture of two or more chlorinated hydrocarbons having a normal boiling point in the range of about 40°-90° C., preferably about 70°-80° C. Preferred chlorinated hydrocarbons are chlorinated paraffins (alkanes). Nonlimiting examples of suitable chlorinated hydrocarbons include dichloromethane, chloroform (trichloromethane), carbon tetrachloride, 1,1-dichloroethane, 1,2-dichloroethane, 1,1,1-trichloroethane, 1,1-dichloropropane, 2,2-dichloropropane, 1-chlorobutane, 2-chloro-2-methylbutane, and mixtures thereof. The presently more preferred chlorinated hydrocarbon is carbon tetrachloride. Generally, the ratio of the weight of the at least one chlorinated hydrocarbon to the combined weight of agents (a), (b) and (c) employed in step (1) is about 4:1 to about 20:1.

Separation step (2) can be carried out in any suitable manner. Preferably, the finished reaction mixture of step (1) is filtered, and the solid filter cake is substantially dried at any suitable conditions, preferably at subatmospheric (i.e., vacuum) conditions, at a temperature of about 25°-60° C. Preferably, step (2) is carried out under a dry inert gas atmosphere ($N_2$, He, Ar, and the like). The finished/dried catalyst particles should be stored under a dry inert gas atmosphere.

The solid composition of matter described above is employed as a catalyst in the alkylation process of this invention. The process for alkylating $C_2$-$C_7$ alkanes (preferably isoalkanes, i.e, branched alkanes) with $C_2$-$C_7$ alkenes (preferably those containing an internal double bond) can be carried out in any suitable manner. The contacting of a mixture of at least one feed alkane and at least one feed alkene, generally at a molar alkane-/alkene ratio of about 1:1 to about 100:1, preferably about 5:1 to about 15:1 (more preferably about 8:1 to about 10:1), with the above-described catalyst composition can be carried out at effective alkylation conditions, preferably at a relatively low temperature of up to about 100° C., preferably about −10° C. to about 100° C., more preferably about 10°-50° C., most preferably about 20°-40° C.; generally at a pressure of about 1-6 atm. (preferably about 1-4 atm.).

The alkane/alkene feed mixture can be contacted with the catalyst composition in any suitable mode, such as in a slurry-type operation in which the catalyst is dispersed in the alkane/alkene feed, or in a fixed catalyst bed operation in which the feed mixture flows downward through a solid catalyst layer, generally at a liquid hourly space velocity of about 0.5-5 $cm^3$ alkane-/alkene feed per $cm^3$ catalyst composition per hour. The alkylation process can be carried as a batch process or in a continuous manner.

Suitable feed alkanes are normal (straight chain) alkanes and isoalkanes (i.e., branched) alkanes, each containing 2-7 carbon atoms per molecule. Non-limiting examples of suitable alkanes are propane, n-butane, isobutane, n-pentane, isopentanes (2-methylbutane and 2,2-dimethylpropane), n-hexane, isohexanes (such as 2-methylpentane, 3-methylpentane, 2,2-dimethylbutane), n-heptane and isoheptanes (such as methyl-substituted hexanes and dimethyl-substituted pentanes). Presently preferred are $C_3$-$C_6$ alkanes, more preferably branched $C_4$-$C_6$ alkanes. Particularly preferred feed alkanes are isobutane and 2-methylbutane.

Suitable feed alkenes are normal (straight chain) and branched alkenes containing one C=C double bond and 2-7 carbon atoms per molecule, preferably those containing an internal C=C double bond (more preferably in the 2 position). Non-limiting examples of suitable alkenes are propylene, butene-1, butene-2, isobutylene, pentene-1, pentene-2, isopentenes, hexene-1, hexene-2, hexene-3 and isohexanes. Preferred alkenes are those containing 3-5 carbon atoms per molecule. The presently more preferred feed alkene is butene-2.

The alkylation process of this invention generally generates a multitude of hydrocarbon products containing a greater number of carbon atoms per molecule than the feed alkane(s), as is demonstrated in the examples. Thus, it is generally necessary to separate the various formed hydrocarbon products from one another and from unconverted feed hydrocarbons. This separation can be carried out in any suitable manner, generally by fractional distillation (possibly in the presence of an extractant, i.e., by extractive distillation, as can be determined by persons skilled in the various liquid-liquid separation technologies.

The following examples are provided to further illustrate the processes of this invention, and are not to be construed as unduly limiting the scope of this invention.

EXAMPLE I

This example illustrates the preparation of various catalyst materials which were employed as catalysts in the alkylation of an alkane (paraffin) with an alkene (monoolefin).

Catalyst A was an $AlCl_3/SiO_2$ control catalyst which was prepared by heating 1.78 grams of dry $AlCl_3$ with 2.50 grams of 60-100 mesh silica (calcined at 600° C. for 3 hours; BET surface area: about 340 $m^2$/g; marketed by the Davison Catalyst Division of W.R. Grace and Company, Baltimore, Md., under the product designation of G-57) and 35 mL of dry carbon tetrachloride for 18 hours under reflux conditions in a dry nitrogen atmosphere. Thereafter, the slurry was cooled and filtered, and the solid catalyst material was dried for several hours under vacuum conditions.

Invention Catalysts B1 through B4 were prepared essentially in the same manner as control Catalyst A, except that boron phosphate was also present during the heating of $AlCl_3$, $SiO_2$ and $CCl_4$: 0.21 g $BPO_4$ for preparing Catalyst B1, 0.26 g $BPO_4$ for preparing Catalyst B2, 0.40 g $BPO_4$ for preparing Catalyst B3 and 0.79 g $BPO_4$ for preparing Catalyst B7. In these four preparations, the weight of $AlCl_3$ was 1.89 g, the weight of $SiO_2$ was 2.50 g, and the volume of $CCl_4$ was 35 mL.

Catalyst C was an $AlCl_3/Al_2O_3$ control catalyst which was prepared by heating 1.78 grams of dry $AlCl_3$ with 2.50 grams of 60-100 mesh alumina (calcined at 500° C. for 4 hours; 1/16" extrudates having a surface area of 281 $m^2$/g and a pore volume of 0.73 cc/g; marketed by Akzo Chemicals, Inc., Chicago, Ill., under the "Ketjen" tradename) and 35 mL of dry $CCl_4$ for 18 hours under reflux conditions in a dry nitrogen atmosphere. The slurry was filtered and dried, as described for Catalyst A.

Invention Catalysts D1 through D6 were prepared essentially in the same manner as Control Catalyst C, except that $BPO_4$ was also present during the heating of $AlCl_3$, $Al_2O_3$ and $CCl_4$: 0.21 g $BPO_4$ for preparing Catalyst D1, 0.27 g $BPO_4$ for preparing Catalyst D2, 0.40 g $BPO_4$ for preparing Catalyst D3, 0.80 g $BPO_4$ for preparing Catalyst D4, 1.06 g $BPO_4$ for preparing Catalyst D5, and 1.41 g $BPO_4$ for preparing Catalyst D6. In these six preparations, the weight of $AlCl_3$ was 1.78 g, the weight of $Al_2O_3$ was 2.5 g, and the volume of $CCl_4$ was 35 mL.

Example II

This example illustrates the use of the catalyst materials described in Example I for the alkylation of isobutane with butene-2.

About 6-7 grams of a feed mixture containing 90 weight-% isobutane and 10 weight-% butene-2 and about 0.5 grams of one of the catalysts described in Example I were placed in a sealed glass flask. The feed/catalyst mixture was maintained at a temperature of about 35°-36° C. and a pressure of about 20 psig, and was agitated with an ultrasound vibrator. After about 0.5 hour, the flask content was analyzed by means of a gas chromatograph. Test results are summarized in Table I.

TABLE I

| Catalyst | Molar BPO$_4$/AlCl$_3$ Ratio | % Conversion of Butene-2 | Liquid Product Composition (Weight-%) | | | | Octane Number[1] |
|---|---|---|---|---|---|---|---|
| | | | C$_4$ Alkanes | C$_5$-C$_7$ Alkanes | C$_8$ Alkanes | C$_9$+ Alkanes | |
| A (Control) | 0 | 96 | 11.9 | 14.3 | 29.1 | 44.8 | 82.4 |
| A (Control) | 0 | 96 | 12.2 | 15.1 | 30.3 | 42.4 | 81.9 |
| A (Control) | 0 | 96 | 12.1 | 14.6 | 29.8 | 43.5 | 82.7 |
| B1 (Invention) | 0.15:1 | 100 | 15.2 | 22.2 | 35.5 | 27.1 | 88.9 |
| B2 (Invention) | 0.19:1 | 100 | 20.4 | 23.6 | 35.5 | 20.4 | 89.0 |
| B3 (Invention) | 1.29:1 | 100 | 21.5 | 25.7 | 33.8 | 18.8 | 89.5 |
| B4 (Invention) | 0.57:1 | 100 | 26.5 | 24.4 | 32.9 | 16.2 | 88.4 |
| C (Control) | 0 | 94 | 12.6 | 13.6 | 28.9 | 45.0 | 80.0 |
| D1 (Invention)[2] | 0.15:1 | 100 | 15.9 | 16.1 | 32.4 | 35.2 | 87.4 |
| D2 (Invention)[2] | 0.20:1 | 100 | 16.0 | 16.4 | 33.6 | 33.6 | 88.6 |
| D3 (Invention)[2] | 0.29:1 | 100 | 15.3 | 19.7 | 35.1 | 29.6 | 88.3 |
| D4 (Invention)[2] | 0.58:1 | 100 | 14.8 | 20.1 | 36.8 | 27.7 | 88.9 |
| D5 (Invention)[2] | 0.77:1 | 100 | 16.6 | 20.3 | 36.1 | 26.3 | 88.1 |
| D6 (Invention)[2] | 1.00:1 | 100 | 16.1 | 20.4 | 34.5 | 28.1 | 87.7 |

[1](research octane no. + motor octane no.) divided by 2
[2]Liquid product also contained about 0.3-0.9 weight-% C$_3$ alkanes Test data in Table I clearly show that the catalyst materials prepared from AlCl$_3$, BPO$_4$ and either SiO$_2$ or Al$_2$O$_3$ were more active as alkylation catalysts and also produced alkylates having higher octane numbers than the catalyst materials prepared from AlCl$_3$ and either SiO$_2$ or Al$_2$O$_3$ (without BPO$_4$).

Reasonable variations, modifications and adaptations for various conditions can be made within the scope of the disclosure and the appended claims without departing from the scope of this invention.

That which is claimed is:

1. A method of preparing a solid composition of matter which comprises the steps of:
   (1) heating for a period of at least about 10 minutes, at a temperature in the range of about 40° C. to about 90° C., in the substantial absence of water: (a) aluminum chloride, (b) boron phosphate, (c) at least one inorganic support material selected from the group consisting of alumina and silica having a surface area of at least about 40 m$^2$/g, and (d) at least one chlorinated hydrocarbon having a normal boiling point of about 40°-90° C.; wherein the molar ratio of boron phosphate to aluminum chloride is at least about 0.1:1, and the weight ratio of boron phosphate to said at least one inorganic support material is at least about 0.05:1; and
   (2) separating the solid component formed in the heated mixture obtained in step (1) from said at least one chlorinated hydrocarbon under a dry gas atmosphere.

2. A method in accordance with claim 1, wherein said at least one chlorinated hydrocarbon employed in step (1) is carbon tetrachloride.

3. A method in accordance with claim 2, wherein the ratio of the weight of said at least one hydrocarbon to the combined weight of agents (a), (b) and (c) in step (1) is about 4:1 to about 20:1.

4. A method in accordance with claim 1, wherein said molar ratio of boron phosphate to aluminum chloride is about 0.1:1 to about 1.0:1 and said at least on inorganic support material is about 0.05:1 to about 1.0:1.

5. A method in accordance with claim 4, wherein said molar ratio of boron phosphate to aluminum chloride is about 0.15:1 to about 1.0:1, and said weight ratio of boron phosphate to said at least one inorganic support material is about 0.08:1 to about 0.6:1.

6. A method in accordance with claim 4, wherein said at least one inorganic support material is alumina having a surface area of about 100-500 m$^2$/g.

7. A method in accordance with claim 4, wherein said at least one inorganic support material is silica having a surface area of about 100-500 m$^2$/g.

8. A method in accordance with claim 1, wherein heating step (1) is carried out for about 5-30 hours under a dry inert gas atmosphere, and step (2) is carried out under an inert gas atmosphere in two sub-steps: filtering the reaction mixture formed in step (1) so as to recover said solid component therefrom, and then drying the recovered solid material.

9. A process for alkylating alkanes which comprises contacting at least one feed alkane containing about 2-7 carbon atoms per molecule with at least one feed alkene containing about 2-7 carbon atoms per molecule with a catalyst composition at effective alkylation conditions so as to obtain at least one product alkane containing at least two more carbon atoms per molecule than said at least one feed alkane; wherein said catalyst composition has been prepared by a method which comprises the steps of:
   (1) beating for a period of at least about 10 minutes, at a temperature in the range of about 40° C. to about 90° C., in the substantial absence of water: (a) aluminum chloride, (b) boron phosphate, (c) at least one inorganic support material selected from the group consisting of alumina and silica having a surface area of at least about 40 m$^2$/g, and (d) at least one chlorinated hydrocarbon having a normal boiling point of about 40°-90° C.; wherein the molar ratio of boron phosphate to aluminum chloride is at least about 0.1:1, and the weight ratio of boron phosphate to said at least one inorganic support material is at least about 0.05:1; and
   (2) separating the solid component formed in the heated mixture obtained in step (1) from said at least one chlorinated hydrocarbon under a dry gas atmosphere.

10. A process in accordance with claim 9, wherein said at least one chlorinated hydrocarbon employed in preparation step (1) is carbon tetrachloride.

11. A process in accordance with claim 10, wherein the ratio of the weight of said at least one hydrocarbon to the combined weight of agents (a), (b) and (c) in step (1) is about 4:1 to about 20:1.

12. A process in accordance with claim 9, wherein said molar ratio of boron phosphate to aluminum chloride is about 0.1:1 to about 1.0:1, and said weight ratio of boron phosphate to said at least on inorganic support material is about 0.05:1 to about 1.0:1.

13. A process in accordance with claim 12, wherein said molar ratio of boron phosphate to aluminum chloride is about 0.15:1 to about 1.0:1, and said weight ratio of boron phosphate to said at least one inorganic support material is about 0.08:1 to about 0.6:1.

14. A process in accordance with claim 12, wherein said at least one inorganic support material is alumina having a surface area of about 100–500 m²/g.

15. A process in accordance with claim 12, wherein said at least one inorganic support material is silica having a surface area of about 100–500 m²/g.

16. A process in accordance with claim 9, wherein heating step (1) is carried out for about 5–30 hours under a dry inert gas atmosphere, and step (2) is carried out under an inert gas atmosphere in two sub-steps: filtering the reaction mixture formed in step (1) so as to recover said solid component therefrom, and then drying the recovered solid material.

17. A process in accordance with claim 9, wherein said effective alkylation conditions comprise a molar feed alkane/alkene ratio of about 1:1 to about 100:1 and a temperature of about $-10°$ C. to about 100° C., and wherein said at least one product alkane contains 3–6 more carbon atoms per molecule than said at least one feed alkane.

18. A process in accordance with claim 17, wherein said molar feed alkane/alkene ratio is about 5:1 to about 15:1, and said temperature is about 10°–50° C.

19. A process in accordance with claim 9, wherein said at least one feed alkane is selected from the group consisting of isobutane and 2-methylbutane, and said at least one feed alkene is butene-2.

20. A composition of matter prepared by the method of claim 1.

* * * * *